(12) United States Patent
Gomperz et al.

(10) Patent No.: US 6,512,959 B1
(45) Date of Patent: Jan. 28, 2003

(54) DOUBLE THREADED STYLET FOR EXTRACTION OF LEADS WITH A THREADED ELECTRODE

(75) Inventors: Benedict L. Gomperz, North Hollywood, CA (US); Russell Klehn, Valencia, CA (US); Sergey Safarevich, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 192 days.

(21) Appl. No.: 09/723,961

(22) Filed: Nov. 28, 2000

(51) Int. Cl.[7] ................................................. A61N 1/05
(52) U.S. Cl. ........................ 607/122; 607/126; 607/127
(58) Field of Search ............................... 607/122, 126, 607/129, 125, 127, 119, 116; 604/158, 159, 105–110

(56) References Cited

U.S. PATENT DOCUMENTS

| | | | |
|---|---|---|---|
| 4,790,825 A | 12/1988 | Bernstein et al. | 604/170 |
| 4,924,881 A | 5/1990 | Brewer | 128/785 |
| 4,943,289 A | 7/1990 | Goode et al. | 606/1 |
| 4,957,118 A | 9/1990 | Erlebacher | 128/785 |
| 4,972,848 A | 11/1990 | Di Domenico et al. | 128/785 |
| 4,988,347 A | 1/1991 | Goode et al. | 606/1 |
| 5,011,482 A | 4/1991 | Goode et al. | 606/1 |
| 5,013,310 A | 5/1991 | Goode et al. | 606/1 |
| 5,020,545 A | 6/1991 | Soukup | 128/785 |
| 5,056,516 A | 10/1991 | Spehr | 128/419 |
| 5,129,404 A | 7/1992 | Spehr et al. | 128/745 |
| 5,207,683 A | 5/1993 | Goode et al. | 606/108 |
| 5,231,996 A | 8/1993 | Bardy et al. | 128/785 |
| 5,234,002 A | 8/1993 | Chan | 128/772 |
| 5,259,395 A | 11/1993 | Li | 607/131 |
| 5,421,348 A | 6/1995 | Larnard | 128/772 |
| 5,447,534 A | 9/1995 | Jammet | 607/127 |
| 5,593,433 A * | 1/1997 | Spehr et al. | 607/128 |
| 5,609,623 A | 3/1997 | Lindegren | 607/128 |
| 6,033,414 A * | 3/2000 | Tockman | 606/129 |
| 6,381,500 B1 * | 4/2002 | Fischer, Sr. | 607/127 |

* cited by examiner

Primary Examiner—Mark Paschall

(57) ABSTRACT

A technique for removing an implanted lead from a body includes the steps of releasably attaching a stylet to both the distal end of the implanted lead and to the proximal end of the implanted lead. This results in a substantially unified stylet and implanted lead structure whereby withdrawal of the stylet and of the implanted lead as a unit facilitates the complete removal of the implanted lead from the body. A threaded tip end may be used for threaded engagement with a tapped bore at the distal end of the implanted lead and at the proximal end, attachment being provided by a threaded region on the stylet distant from the threaded tip end for threaded engagement with a tapped bore of a connector pin integral with the implanted lead. In this instance, the diameter of the proximal threaded region on the stylet is greater than that of the threaded tip end. In one embodiment, the implanted lead is resiliently extensible and the stylet is greater in length than the implanted lead in its relaxed condition and tension is applied to the proximal end of the implanted lead to thereby stretch it so that the proximal end of the implanted lead is generally coextensive with the proximal end of the stylet.

7 Claims, 6 Drawing Sheets

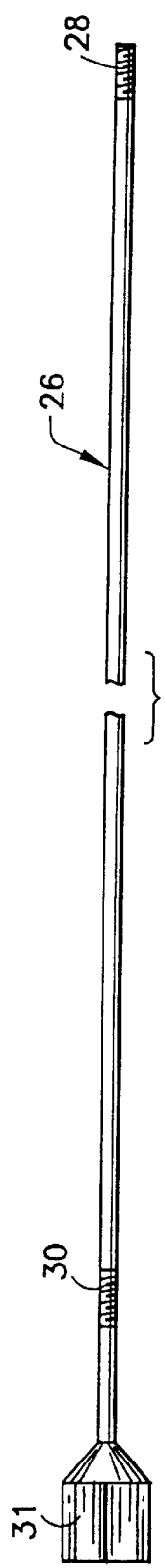
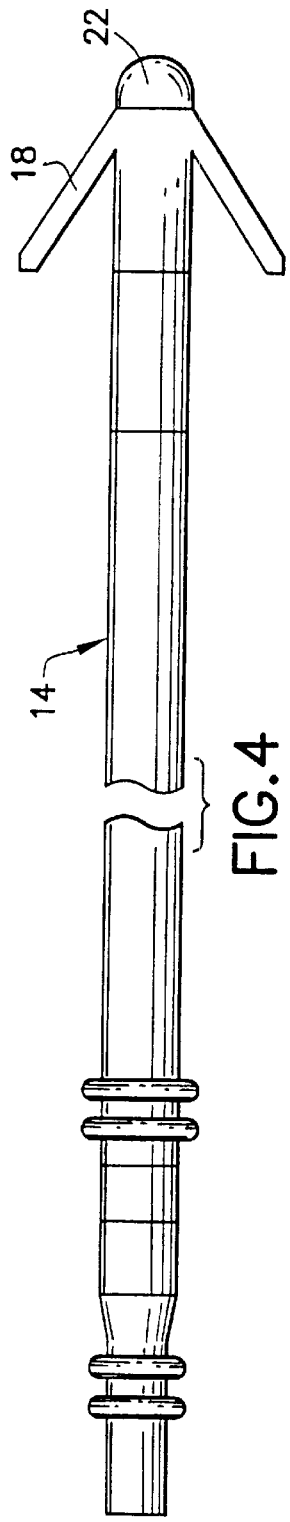
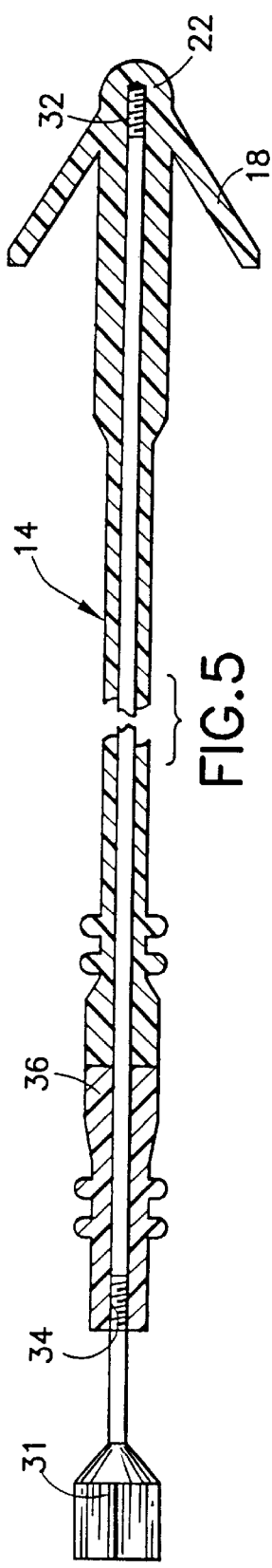
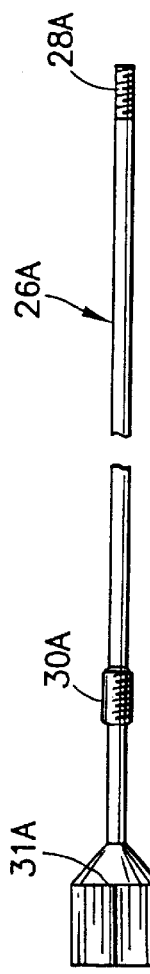

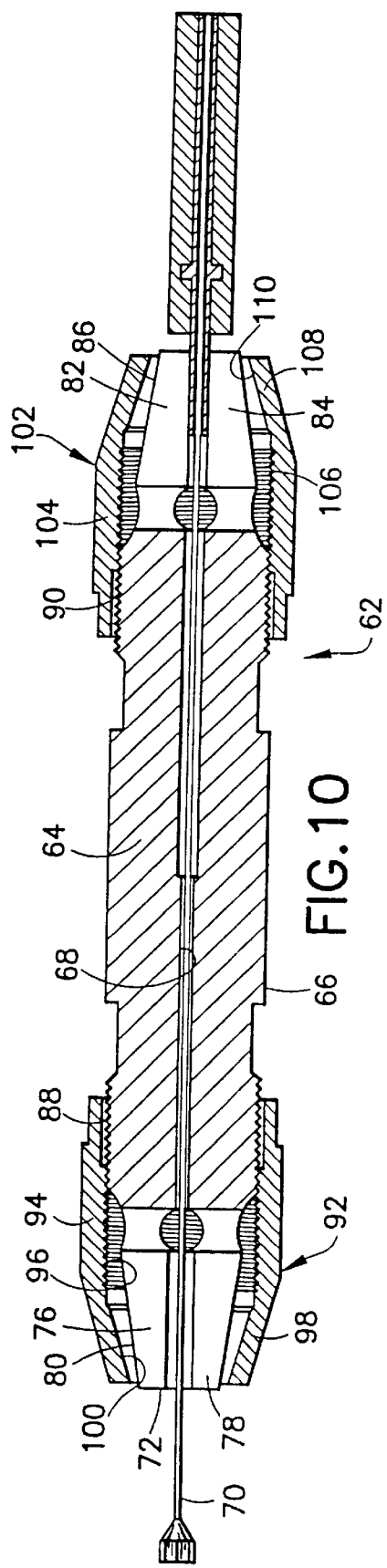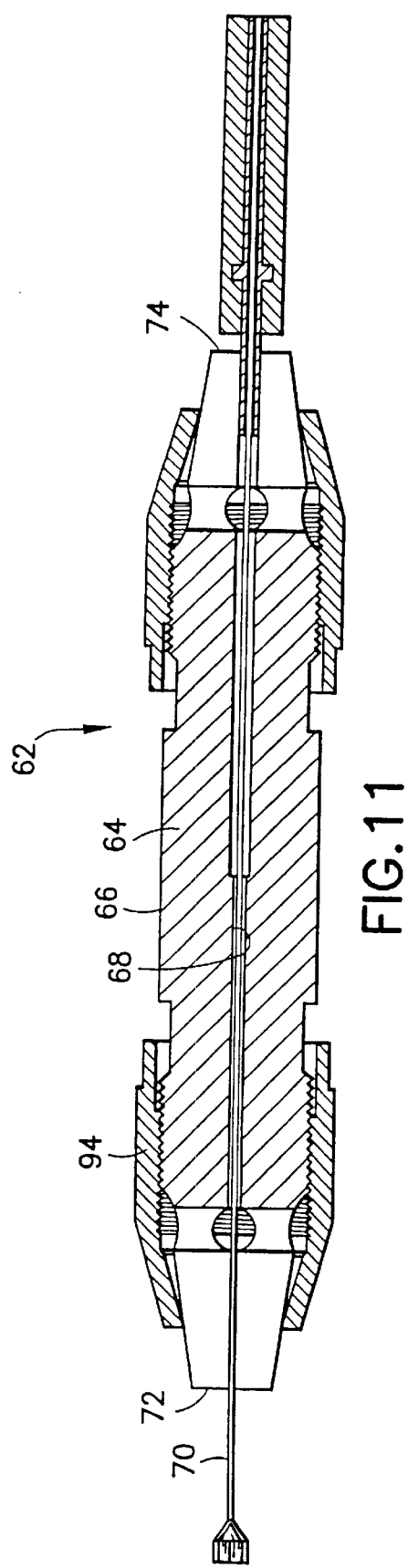
FIG. 10
FIG. 11

DOUBLE THREADED STYLET FOR EXTRACTION OF LEADS WITH A THREADED ELECTRODE

FIELD OF THE INVENTION

The present invention relates generally to implantable cardiac stimulation leads, more specifically to removal of an implanted lead extending between distal and proximal ends from a body and, still more particularly, to a technique which facilitates the complete removal of the lead from the body.

BACKGROUND OF THE INVENTION

Lead extraction is required when an infection occurs and at times when products are upgraded or replaced. Current lead extraction techniques cut the connector from the lead, then mechanically lock into the lead conductor coil near the lead distal electrode. During the lead extraction, the distal end of the coil is deformed and the lead is no longer functional. There is a potential for lead fracture, resulting in incomplete extraction, and possibly additional surgery to complete the procedure.

Typical of the known prior art are U.S. Pat. Nos. 5,013,310 and 5,011,482, both to Goode et al., which utilize a stylet wire which is inserted into the longitudinal passageway of an implanted lead, then secured at its distal end to the distal end of the implanted lead. Thereafter, the stylet wire is withdrawn and takes with it the implanted lead. U.S. Pat. No. 4,957,118 represents another example of the prior art in which an electrode lead is provided with a tine assembly having tines on an electrode tip which can be moved back and forth between a retracted position and an extended position. A threaded rod is rotatably mounted within the elongated body of the lead for moving the conductive electrode tip relative to the non-conductive tubular body. In a number of instances, as in U.S. Pat. No. 4,924,881 to Brewer, an implantable endocardial lead includes a retractable fixation device such as a sharpened helix. A threaded stylet passes through a lumen from a proximal end to a distal end of the lead where the stylet is screwed into a piston supporting the helix. When the helix is in an exposed position, torque can be transmitted by the stylet from the proximal end of the lead through the distal end to the piston and thence to the helix to screw the helix into the endocardial tissue. Similar constructions are disclosed in U.S. Pat. Nos. 5,129,404 and 5,593,433 to Spehr et al. and in U.S. Pat. No. 5,259,395 to Li.

It was in light of the foregoing that the present invention was conceived and has now been reduced to practice.

SUMMARY OF THE INVENTION

The present invention discloses a technique for removing an implanted lead from a body includes the steps of releasably attaching a stylet to both the distal end of the implanted lead and to the proximal end of the implanted lead. This results in a substantially unified stylet and implanted lead structure whereby withdrawal of the stylet and of the implanted lead as a unit facilitates the complete removal of the implanted lead from the body. A threaded tip end may be used for threaded engagement with a tapped bore at the distal end of the implanted lead and at the proximal end, attachment being provided by a threaded region on the stylet distant from the threaded tip end for threaded engagement with a tapped bore of a connector pin integral with the implanted lead. In this instance, the diameter of the proximal threaded region on the stylet is greater than that of the threaded tip end. In one embodiment, the implanted lead is resiliently extensible and the stylet is greater in length than the implanted lead in its relaxed condition and tension is applied to the proximal end of the implanted lead to thereby stretch it so that the proximal end of the implanted lead is generally coextensive with the proximal end of the stylet.

According to the technique, a stylet extends between distal and proximal attachment members, the distal attachment member being releasably attachable to the distal end of the implantable lead and the proximal attachment member being releasably attachable to the proximal end of the lead. This construction results in a substantially unified stylet and lead structure whereby withdrawal of the stylet and of the lead as a unit is essentially assured.

The new lead extraction method mechanically locks the stylet into the lead distal tip and the proximal end to provide force and control at the location where the lead adheres to the myocardium and creates a pulling action on the lead in addition to the force at the tip. The method also reduces the friction between the lead body and the vessel. This method stretches the lead and in the process reduces the lead body diameter. This invention will improve lead extraction in the form of fewer lead fractures, and no lead fragments left in the heart as compared to existing lead extraction systems.

Inserting the extraction stylet would not require that the lead connector be cut off. If a decision is made to abort the lead removal, the double threaded stylet can be unscrewed, leaving the lead unchanged.

In the resiliently extensible embodiment, a double threaded stylet stretches the lead during extraction by threading into both ends of the lead. The stretching is accomplished by threading the stylet into the distal end of the lead, then pulling the lead against the stylet and fixing the proximal end of the lead to the stylet. The following benefits flow from the invention:

1. the lead can be elongated, reducing the lead body diameter;
2. the lead can be pulled from the connector end and simultaneously from the distal tip in a longitudinal direction during extraction;
3. the lead will be captured between threaded sections at the distal tip and the connector pin; therefore, the lead should not fracture and certainly will be removed in its entirety; and
4. these features can be added to all implantable cardiac leads.

Three lead components, namely, the stylet, the distal tip, and the connector pin, may be different than the components typically used in cardiac leads. The stylet is threaded at the distal end of the lead for locking into the distal tip of the lead, and a second thread is proximal to where the connector pin of the lead is located when the stylet is threaded into the distal tip. The distal tip has an internal thread for the purpose of receiving the threaded stylet. The connector pin has a thread that is designed to be mated with the proximal thread on the modified stylet.

A primary feature, then, of the present invention is the provision of a technique for removal from a body of an implanted lead extending between distal and proximal ends.

Another feature of the present invention is the provision of such a technique, which facilitates the complete removal of the lead from the body.

Still another feature of the present invention is the provision of such a technique according to which a stylet extends between distal and proximal attachment members, the distal attachment member being releasably attachable to the distal end of the implantable lead and the proximal attachment member being releasably attachable to the proximal end of the lead, resulting in a substantially unified stylet and lead structure whereby withdrawal of the stylet and of the lead as a unit is essentially assured.

Yet another feature of the present invention is the provision of such a technique according to which lead extraction is achieved by mechanically engaging the distal tip and proximal connectors, eliminating the possibility of lead fracture and partial lead extraction.

Still a further feature of the present invention is the provision of such a technique according to which lead extraction can be aborted, leaving the lead unchanged.

Yet a further feature of the present invention is the provision of such a technique according to which cutting of the lead at the connector is not required as is currently required by known methods.

Still another feature of the present invention is the provision of such a technique according to which a lead and a stylet are locked together at the proximal and distal ends so that the lead can be pulled from the connector end and simultaneously from the distal tip in a longitudinal direction during extraction.

Yet another feature of the present invention is the provision of such a technique according to which the lead diameter is reduced during extraction which reduces the friction between the lead and the vessel from which it is being extracted.

Yet a further feature of the present invention is the provision of such a technique according to which a known implant method and stylet will function properly with leads incorporating the novel concept of the invention.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

BRIEF DESCRIPTION OF THE DRAWINGS

FIG. 3 is a side elevation view of a stylet constructed according to the present invention.

FIG. 4 is a side elevation view of an implantable lead in a relaxed condition.

FIG. 5 is a side elevation view of the implantable lead of FIG. 4 in an elongated condition caused by a stylet with which it is here combined.

FIG. 6 is a side elevation view, similar to FIG. 3, illustrating another embodiment of stylet according to the invention.

FIGS. 10 and 11 are side elevation views, cut away and in section, illustrating two different positions of parts of the combination illustrated in FIG. 9.

DETAILED DESCRIPTION OF THE PREFERRED EMBODIMENTS

Figure 1:
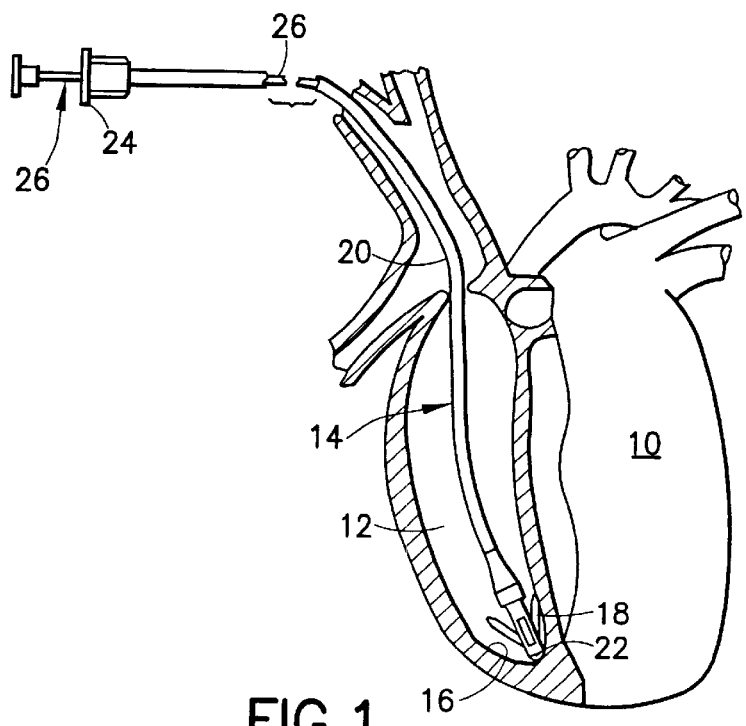
FIG. 1 is a is a perspective view illustrating a heart with a portion cut away to reveal an implantable lead assembly, embodying the present invention, secured therein to a wall of the heart.
Figure 2:
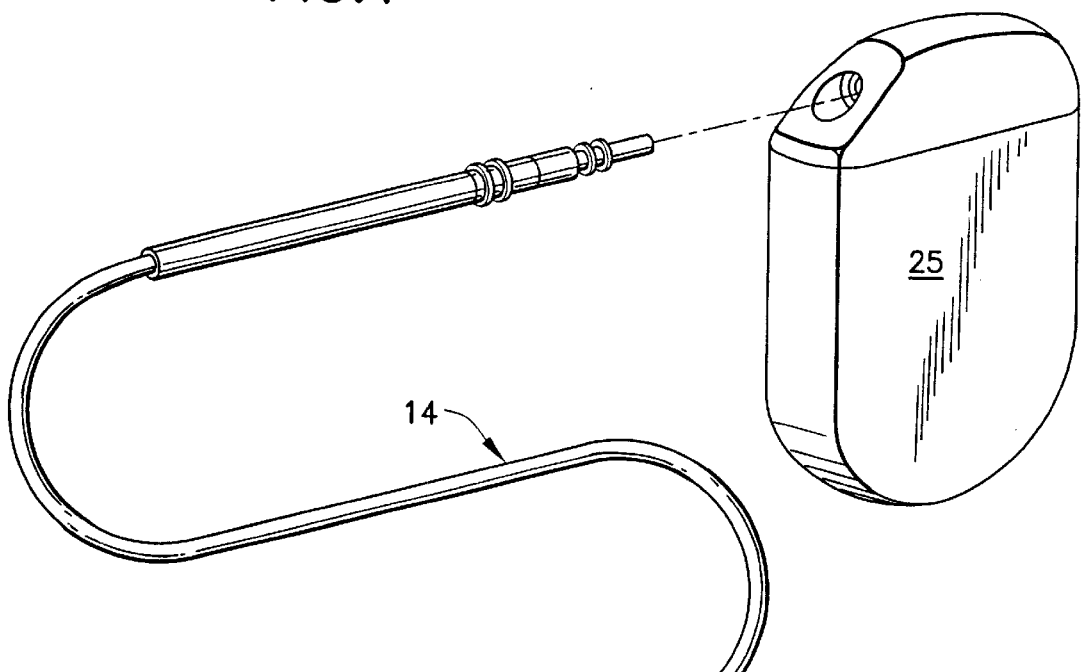
FIG. 2 is a is a perspective view of an implantable lead embodying the invention in combination with a stimulating device such as a pacemaker.

In FIG. 1, there is shown a diagrammatic perspective view partially cut away and shown in section of a heart 10 into the left ventricle 12 of which is inserted a body implantable lead 14 of the endocardial type incorporating features of the present invention. Although the present invention will be described with reference to the single embodiment shown in the drawings, it should be understood that the present invention can be embodied in many alternate forms of embodiments. In addition, any suitable size, shape or type of elements or materials could be used. The lead 14 is attached to an interior wall 16 of the heart 10 by means of fixing tines 18, which engage the tissue or trabeculae of the heart. As further illustrated, the lead 14 also includes tubing 20 interconnecting a distal electrode 22 secured adjacent to the interior wall 16 and a proximal end 24 to which can be attached a source of electrical energy such as a pacemaker 25 (FIG. 2). In FIG. 1, a stylet 26 is illustrated inserted within the tubing 20 and may be used to provide rigidity to the 20 during insertion of the lead 14 into the heart 10. However, in the present instance, concern is for removing the implanted lead 14 from a body or, more specifically, from an organ such as the heart 10.

To this end, viewing FIGS. 3–5, the stylet 26 is illustrated in FIG. 3 as extending between a distal attachment device, such as a threaded tip end 28 and a proximal attachment device which includes a threaded region 30 on the stylet distant from the threaded tip end. A finger grip 31 at a proximal extremity of the stylet 26 is provided for manipulating the stylet and the lead 14. The threaded tip end 28 is provided for threaded engagement with a tapped bore 32 at the distal end of the implanted lead 14. The threaded region 30 of the proximal attachment device is threadedly engageable with a tapped bore 34 (FIG. 5) of a connector pin 36 integral with the implanted lead 14 at its proximal end. When the stylet is so joined to the lead, the result is a substantially unified stylet and implanted lead structure whereby withdrawal of the stylet and of the implanted lead as a unit facilitates the complete removal of the implanted lead from the body.

FIG. 4 depicts the stimulating lead 14 before elongation and FIG. 5 depicts the lead 14 after elongation with the stylet threaded into the distal tip and the proximal connector pin of the lead. The stylet threads are sufficiently spaced to achieve this measure of elongation. It will be appreciated that elongating the lead reduces its diameter from that indicated diagrammatically in FIG. 4 to that indicated in FIG. 5. By connecting both ends of the lead to the stylet under tension, during lead extraction, consistent pulling force will be applied in the direction of lead extraction from both ends of the lead simultaneously. Also, the reduction in diameter will reduce the friction between the lead body and the venous structure from which it is being extracted.

In FIG. 6, a modified stylet 26A is illustrated with a proximal threaded region 30A having a diameter greater than that of a threaded tip end 28A. This stylet functions in a manner similar to that of the FIG. 3 embodiment except that the threaded tip end 28A can be passed through the connector pin 36 without needing to be threaded. For this stylet, the lead 14 would need an internal thread in the distal tip and the connector pin.

Figure 7:
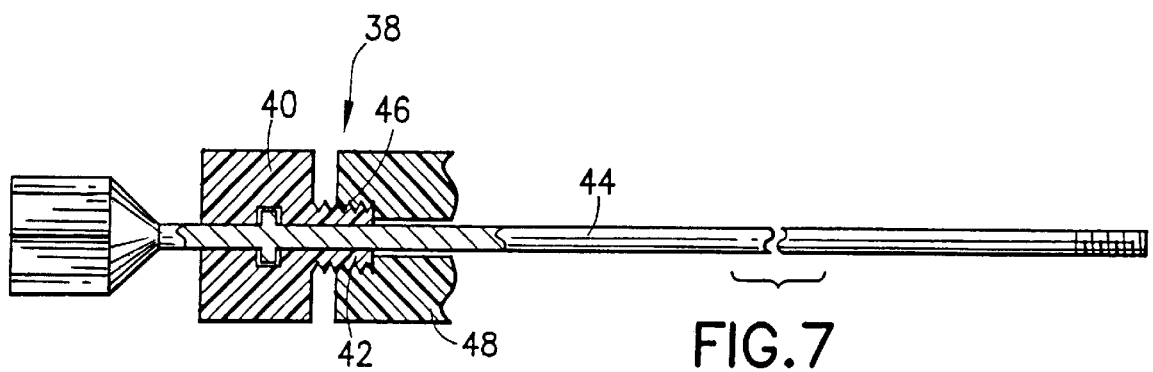
FIGS. 7 and 8 are side elevation views, respectively, of different embodiments of combinations of stylets and proximal attachment members according to the invention.

Another embodiment is illustrated in FIG. 7. In this instance, a proximal attachment member 38 includes a nut member 40, which has an integral distally extending threaded stud 42. The nut member is journaled for rotation about a longitudinal axis of a stylet 44 while being prevented from longitudinal movement along the stylet. The threaded stud 42 is threadedly engageable with a tapped bore 46 of a connector pin 48 integral with the implanted lead at the proximal end of the implanted lead.

Figure 8:
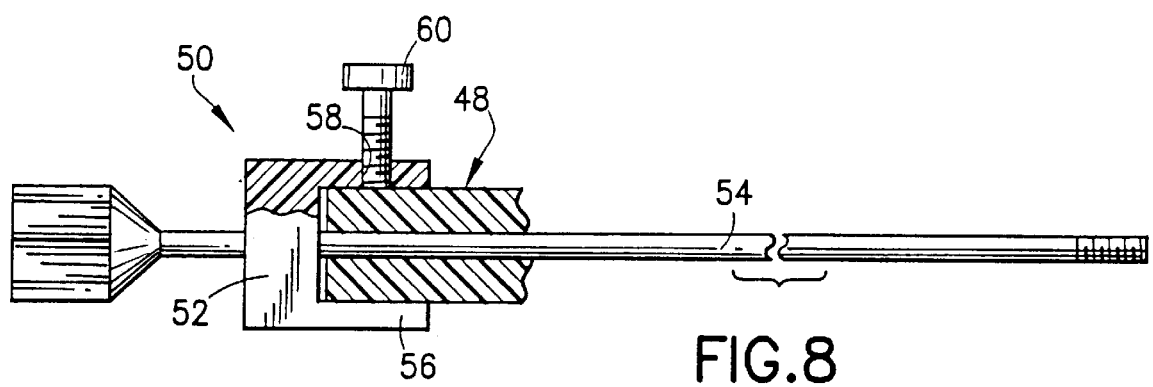

Still another embodiment is illustrated in FIG. 8. In this instance, a proximal attachment member 50 includes a base member 52 integral with a modified stylet 54 and projecting radially from the stylet. A distally extending cylindrical flange member 56 is coaxial with the stylet 54 and is formed with a radially directed tapped bore 58 at a location spaced from the base member 52. A setscrew 60 is threadedly received in the tapped bore 58 for fixation of the proximal end of the implanted lead. Again, this embodiment allows for the stylet 54 to be engaged into the distal tip of the lead first. Then, the lead connector end can be pulled and the stylet setscrew is turned to lock onto the connector pin 48 in the locked position. For this stylet, the lead would only need an internal thread in the distal tip.

Figure 9:
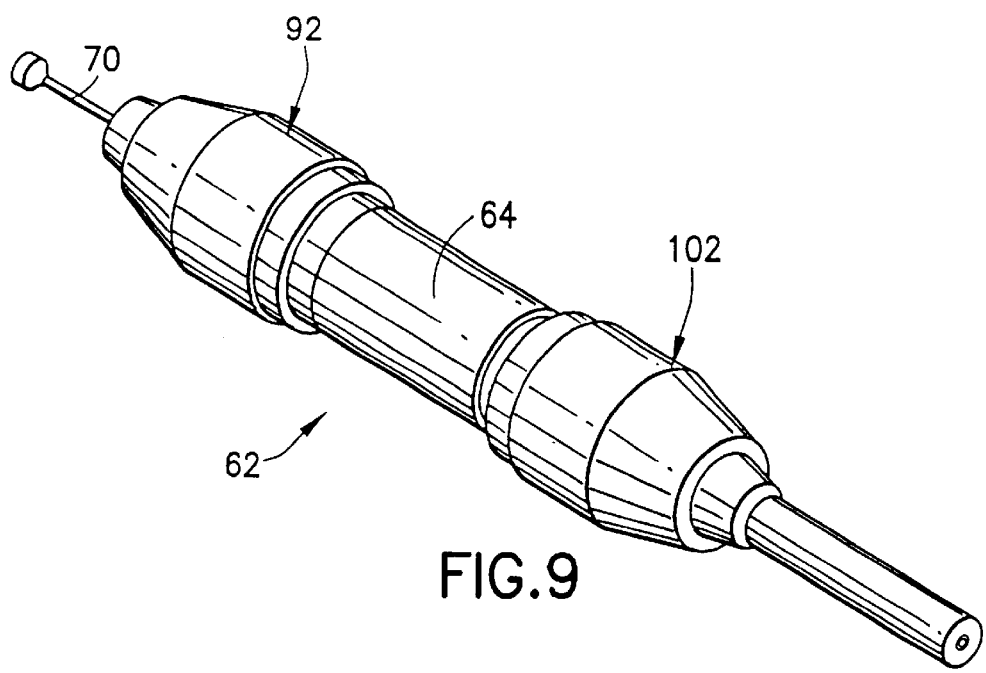
FIG. 9 is a detailed perspective view of another embodiment of a combination of stylet and proximal attachment member according to the invention.

Still another embodiment is illustrated in FIGS. 9, 10, and 11. In this instance, a proximal attachment member 62 includes a stylet clamp 64 having an outer peripheral surface 66 and a longitudinally extending bore 68 for slidable reception of a stylet 70. The stylet clamp 64 extends between proximal and distal tip ends 72, 74, respectively. Integral with the stylet clamp and projecting to the proximal tip end 72 are first laterally opposed and normally spaced apart jaw members 76, 78, each jaw member having a conical outer peripheral surface 80 of reduced diameter with increasing distance toward the proximal tip end. Similarly, integral with the stylet clamp 64 and projecting to the tip end 74 are second laterally opposed and normally spaced apart jaw members 82, 84, each jaw member having a conical outer peripheral surface 86 of reduced diameter with increasing distance toward the distal tip end.

Proximal screw threads 88 are formed on the outer peripheral surface 66 of the stylet clamp 64 spaced from the proximal tip end 72 and distal screw threads 90 are formed on the outer peripheral surface of the stylet clamp spaced from the distal tip end 74.

A proximal tubular clamp cap 92 has a cylindrical section 94 with a tapped internal bore 96 threadedly engaged with the proximal screw threads 88. Additionally, the proximal tubular clamp cap 92 has a proximally projecting conical section 98 extending to a proximal opening 100 having a smaller diameter than that of the cylindrical section 94. In similar fashion, a distal tubular clamp cap 102 has a cylindrical section 104 with a tapped internal bore 106 threadedly engaged with the distal screw threads 90. Additionally, the distal tubular clamp cap 102 has a distally projecting conical section 108 extending to a distal opening 110 having a smaller diameter than that of the cylindrical section 104.

With this construction, as the proximal clamp cap 92 is rotated relative to the stylet clamp 64 for advancement in a direction away from the proximal tip ends 72 of the jaw members 76, 78, the proximal opening 100 of the conical section 98 of the proximal clamp cap 92 engages the outer peripheral surface 80 of the jaw members and forces them into engagement with a proximal end of the stylet 70 received between the jaw members. In a similar manner, as the distal clamp cap 102 is rotated relative to the stylet clamp 64 for advancement in a direction away from the distal tip ends 74 of the jaw members 82, 84, the distal opening 110 of the conical section 108 of the distal clamp cap 102 engages the outer peripheral surface 86 of the jaw members and forces them into engagement with the distal end of the stylet 70 received between the jaw members.

The proximal attachment member 62 attaches to the lead connector pin and to the stylet. At the distal end of the lead, the stylet is attached in the same manner as illustrated in the earlier embodiments discussed. Therefore, the proximal attachment member is only utilized for attaching the stylet to the lead at one location. To utilize the proximal attachment member, the distal end of the proximal attachment member is first attached to the connector pin of the lead. Second, the proximal attachment member is pulled along the stylet in the proximal direction, creating tension in the lead. Then, the proximal attachment member is attached to the stylet.

Turn now to FIGS. 12–16 for a description of various distal electrode thread designs, which are suitable for the present invention.

Figure 12:
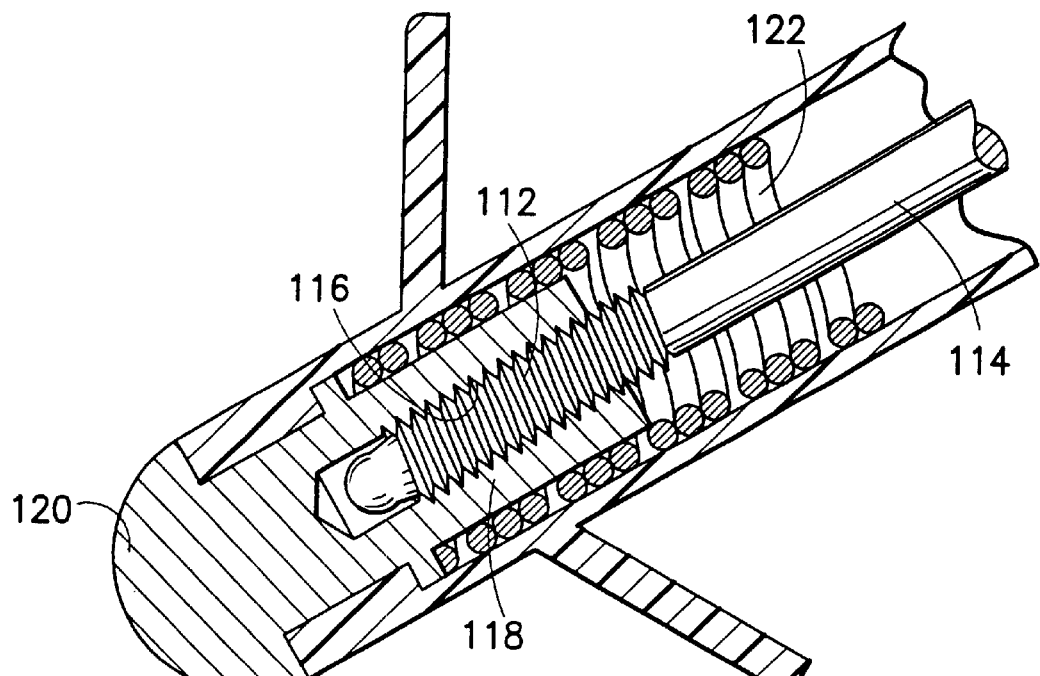
FIGS. 12–16 are detail cross-section views of the distal ends of different embodiments of implantable leads embodying the invention.

In the instance illustrated in FIG. 12, a tapped end 112 of a stylet 114 is screwed into a threaded bore 116 of a weld electrode 118 and the weld electrode is welded to a distal electrode 120. The present invention applies force directly to the distal tip electrode compared to the current stylets for lead extraction systems that lock onto a conductor coil 122. This extraction stylet 114 can also be removed, by unscrewing, from the distal tip electrode if a decision is made to abort the lead extraction. When the stylet is unscrewed, neither the weld electrode 118 nor the conductors 122 are damaged, and the stylet is removed in whole.

Figure 13:
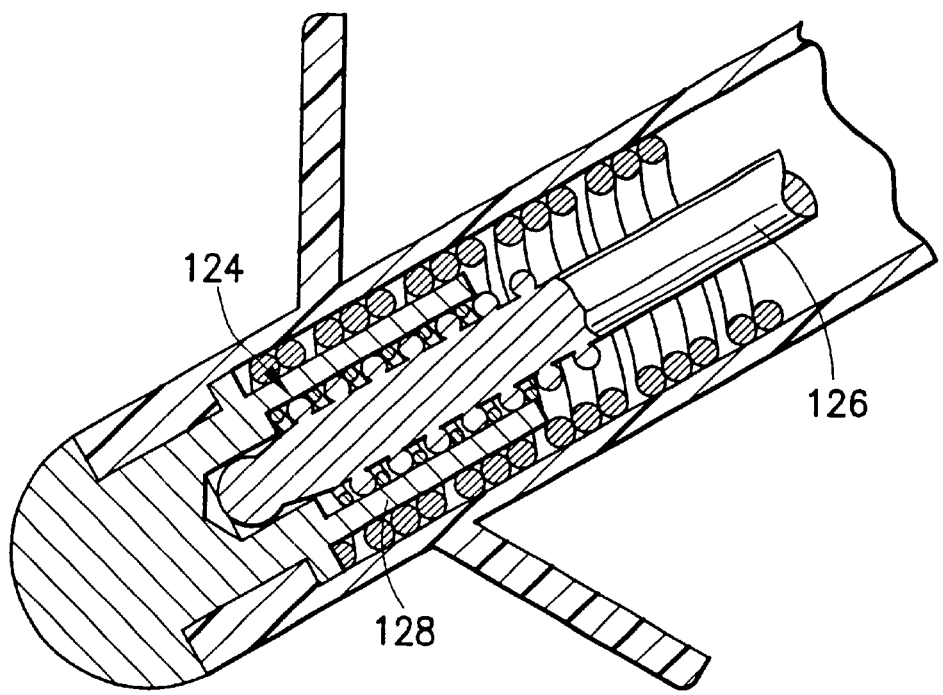

In the instance illustrated in FIG. 13, an alternative embodiment to that shown in FIG. 12, threads 124 are shown as helical coils that are joined to the stylet 126 and the weld electrode 128.

Figure 14:
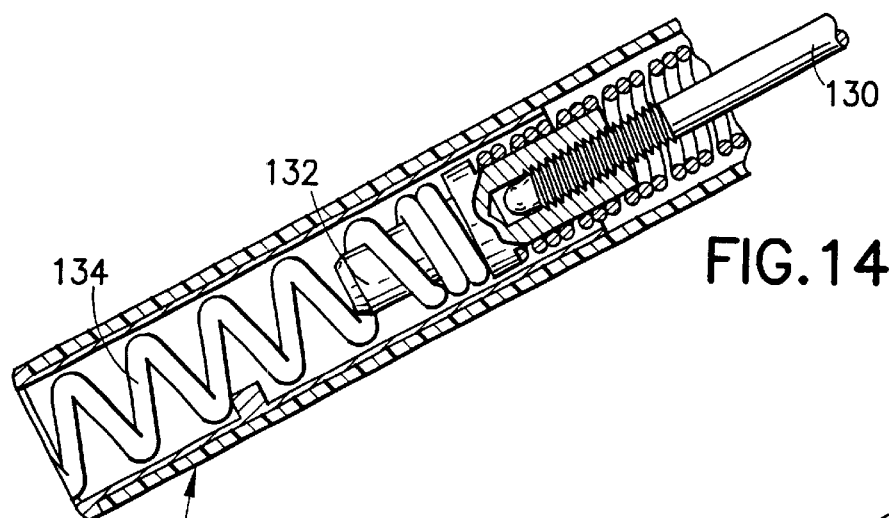

The embodiment illustrated in FIG. 14 applies to an active fixation lead 129 and according to which a stylet 130 is threadedly connected to a distal electrode 132 provided with a fixing helix 134. With the stylet 130 thereby connected, the extraction process can proceed.

Figure 15:
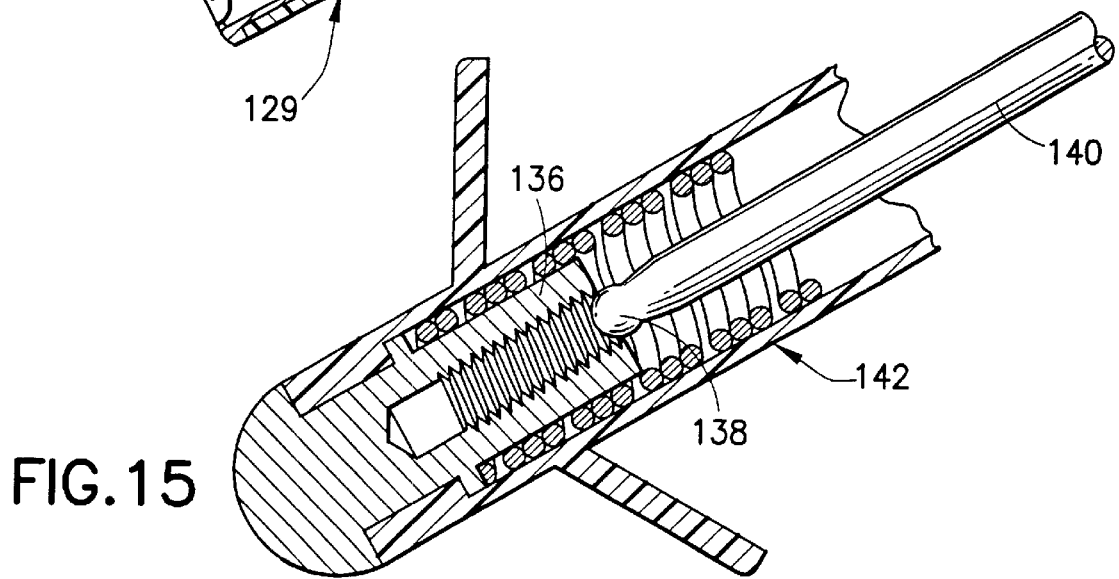

In the instance illustrated in FIG. 15, a tapped weld electrode 136 is shown to be smaller than a ball tip 138 of a stylet 140 representing a current standard stylet. This embodiment allows a lead 142 to be implanted with a standard stylet without requiring new parts or techniques. In addition, the threads of the tapped weld electrode 136 are not damaged during the use of the standard stylet, so the functionality of the lead extraction stylet and mechanism is maintained.

Figure 16:
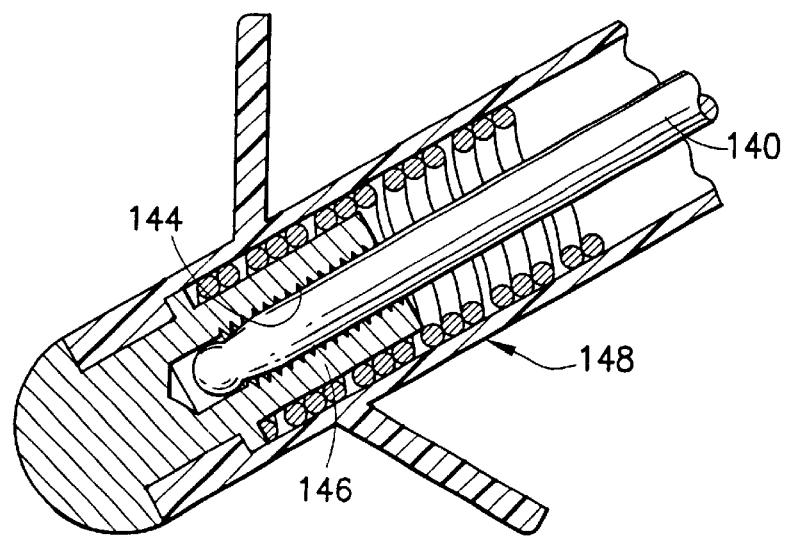

FIG. 16 illustrates an alternative use of the standard stylet 140. A tapped thread 144 of a weld electrode 146 has a larger diameter than the standard ball-tipped stylet 140. Again, a lead 148 so constructed may be implanted with the standard stylet 140 without damaging the threads 144 for the lead extraction system.

It should be understood that the foregoing description is only illustrative of the invention. Various alternatives and modifications can be devised by those skilled in the art without departing from the invention. Accordingly, the present invention is intended to embrace all such alternatives, modifications and variances, which fall within the scope of the appended claims.

What is claimed is:

1. An implantable lead system having means for removing an implantable lead from a patient's body, comprising:
   an implanted lead extending between a distal end implanted in the body and a proximal end;
   distal attachment means at the distal end of the implanted lead;
   proximal attachment means at the proximal end of the implanted lead;
   a stylet extending between distal attachment means releasably attachable to the distal end of the implanted lead and proximal attachment means releasably attachable to the proximal end of the implanted lead and resulting in a substantially unified stylet and implanted lead structure whereby withdrawal of the stylet and of the implanted lead as a unit facilitates the complete removal of the implanted lead from the body.

2. The lead system, as set forth in claim 1, wherein:
   the implanted lead includes a resiliently extensible tubular member; and
   the stylet is greater in length than the implanted lead in its relaxed condition and substantially nonextensible such that when the distal attachment means is releasably attached to the distal attachment means of the implanted lead and when the proximal attachment means is releasably attached to the proximal attachment means of the implanted lead, the implanted lead is stretched taut resulting in a substantially unified stylet and implanted lead structure.

3. The lead system, as set forth in claim 1, wherein:
   the distal attachment means includes a threaded tip end for threaded engagement with a tapped bore at the distal end of the implanted lead; and
   the implanted lead includes an integral connector pin having a tapped bore at the proximal end thereof; and
   the proximal attachment means includes a threaded region on the stylet distant from the threaded tip end for threaded engagement with the tapped bore of the connector pin.

4. The lead system, as set forth in claim 3, wherein:
   the diameter of the threaded region on the stylet is greater than that of the threaded tip end.

5. The lead system, as set forth in claim 1, wherein:
   the implanted lead includes an integral connector pin at the proximal end thereof with a longitudinally extending proximally facing tapped bore therein; and
   the proximal attachment means includes a nut member having an integral distally extending threaded stud, the nut member being journaled for rotation about a longitudinal axis of the stylet while prevented from longitudinal movement along the stylet, the threaded stud being threadedly engageable with the tapped bore of the connector pin.

6. The lead system, as set forth in claim 1, wherein the proximal attachment means comprises:
   a distally extending flange member with a radially directed tapped bore therein; and
   a setscrew threadedly received in the tapped bore of the flange member for engagement with the proximal end of the implanted lead.

7. The lead system, as set forth in claim 1, wherein:
   the implanted lead is a resiliently extensible implanted lead whose distal end is implanted in the body;
   the stylet is greater in length than the implanted lead in its relaxed condition; and
   a substantially unified stylet and implanted lead structure results when tension is applied to the proximal end of the implanted lead to thereby stretch it to substantially the length of the stylet, whereby withdrawal of the stylet and of the implanted lead as a unit facilitates the complete removal of the implanted lead from the body.

* * * * *